(12) United States Patent
Ueno et al.

(10) Patent No.: US 7,488,949 B2
(45) Date of Patent: Feb. 10, 2009

(54) RADIOLOGICAL IMAGING APPARATUS AND ITS COOLING SYSTEM

(75) Inventors: Yuuichirou Ueno, Hitachi (JP); Kensuke Amemiya, Hitachinaka (JP); Norihito Yanagita, Hitachi (JP); Takafumi Ishitsu, Hitachi (JP); Keiji Kobashi, Mito (JP); Tomoyuki Seino, Hitachi (JP); Katsutoshi Tsuchiya, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 52 days.

(21) Appl. No.: 11/206,902

(22) Filed: Aug. 19, 2005

(65) Prior Publication Data

US 2006/0065848 A1   Mar. 30, 2006

(30) Foreign Application Priority Data

Sep. 30, 2004   (JP)   ............................. 2004-288406

(51) Int. Cl.
*G01T 1/24*   (2006.01)
(52) U.S. Cl. .............................................. 250/370.15
(58) Field of Classification Search ............ 250/370.15, 250/370.01, 370.08, 370.09; 378/199, 200
See application file for complete search history.

(56) References Cited

U.S. PATENT DOCUMENTS

| | | | | |
|---|---|---|---|---|
| 4,274,005 A * | 6/1981 | Yamamura et al. ............. 378/9 |
| 4,456,826 A * | 6/1984 | Forster ................... 250/370.09 |
| 4,831,639 A * | 5/1989 | Harke ........................... 378/19 |
| 4,969,167 A * | 11/1990 | Zupancic et al. .............. 378/19 |
| 5,991,357 A * | 11/1999 | Marcovici et al. ............. 378/19 |
| 6,236,051 B1 * | 5/2001 | Yamakawa et al. ........ 250/370.1 |
| 6,472,668 B1 | 10/2002 | Griesmer et al. |
| 6,586,744 B1 * | 7/2003 | Griesmer et al. ........ 250/370.15 |
| 6,621,084 B1 * | 9/2003 | Wainer et al. ........... 250/370.09 |
| 6,931,092 B2 * | 8/2005 | Joshi et al. ..................... 378/19 |
| 7,045,790 B2 * | 5/2006 | Shoji ...................... 250/370.15 |
| 7,065,173 B2 * | 6/2006 | Lacey et al. .................... 378/19 |
| 7,145,153 B2 * | 12/2006 | Beekman ..................... 250/393 |
| 7,217,931 B2 * | 5/2007 | Ueno et al. ............. 250/370.09 |
| 7,261,466 B2 * | 8/2007 | Bhatt et al. ................... 378/199 |
| 2004/0234023 A1 * | 11/2004 | Kollegal et al. ................ 378/10 |

(Continued)

FOREIGN PATENT DOCUMENTS

JP   09-276262   10/1997

(Continued)

OTHER PUBLICATIONS

Lecomte, R., et al., "Design and Engineering Aspects of Avalanche Photodiode PET Tomograph," IEEE (1994), pp. 1063-1067.

*Primary Examiner*—David P Porta
*Assistant Examiner*—David S Baker
(74) *Attorney, Agent, or Firm*—Dickstein Shapiro LLP

(57) ABSTRACT

A radiological imaging apparatus including a bed which supports an object to be examined and an imaging apparatus, wherein the imaging apparatus has a unit substrate including a first substrate including a radiation detector and a second substrate including a signal processing apparatus to which detection signals of the radiation detector are inputted and the first substrate is connected through a connector, and is provided with a heat insulating member of separating mutually a first area where the radiation detector is disposed from a second area where the signal processing apparatus is disposed, both of which are formed inside the imaging apparatus.

6 Claims, 7 Drawing Sheets

U.S. PATENT DOCUMENTS

2005/0067579 A1* 3/2005 Tsuchiya et al. ....... 250/370.15
2006/0241386 A1* 10/2006 Yanagita et al. ............. 600/415
2007/0080296 A1* 4/2007 Ueno et al. ............ 250/363.04
2007/0284535 A1* 12/2007 Heismann et al. ...... 250/370.15

FOREIGN PATENT DOCUMENTS

JP   10-160847   6/1998

* cited by examiner

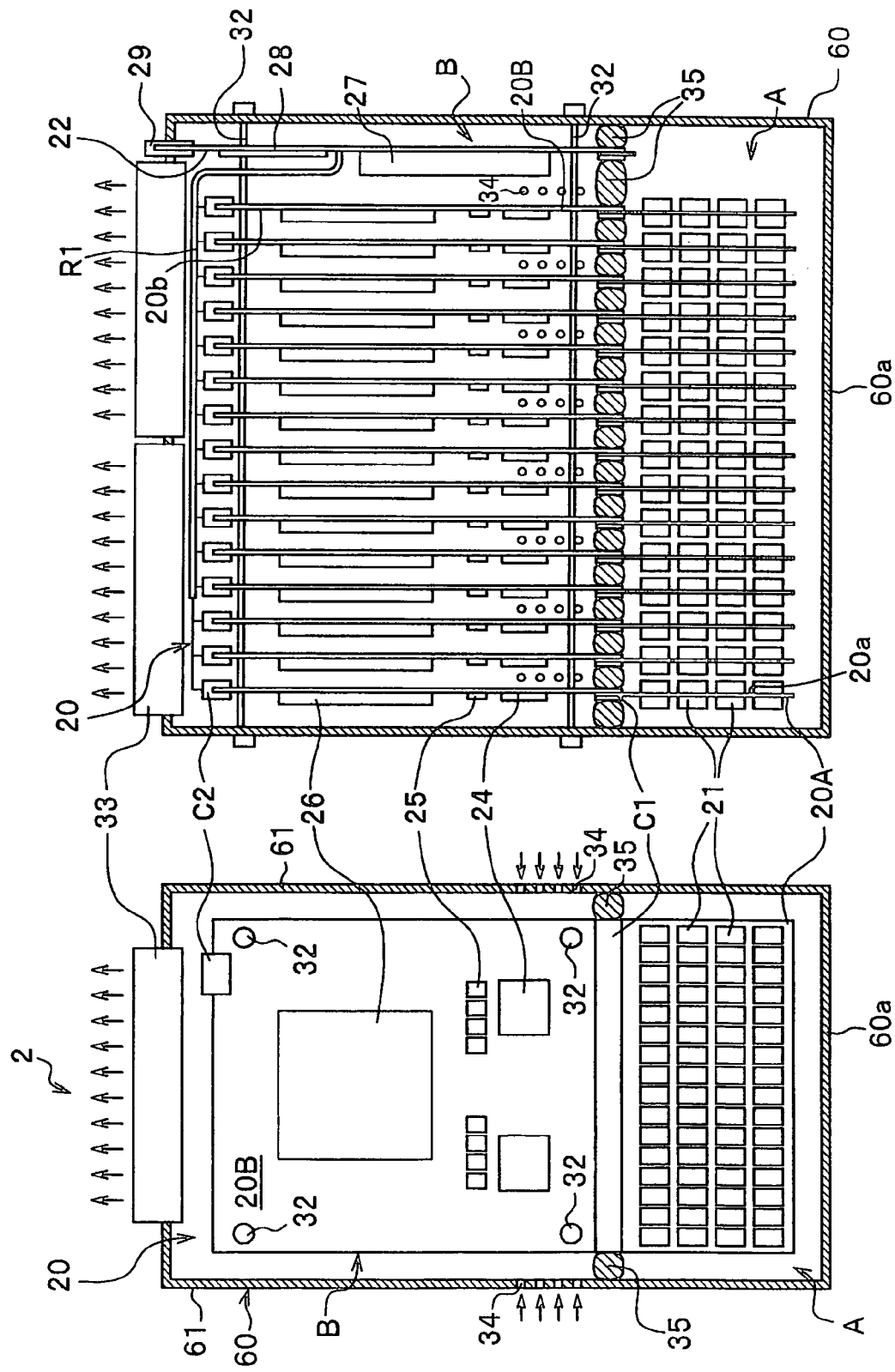

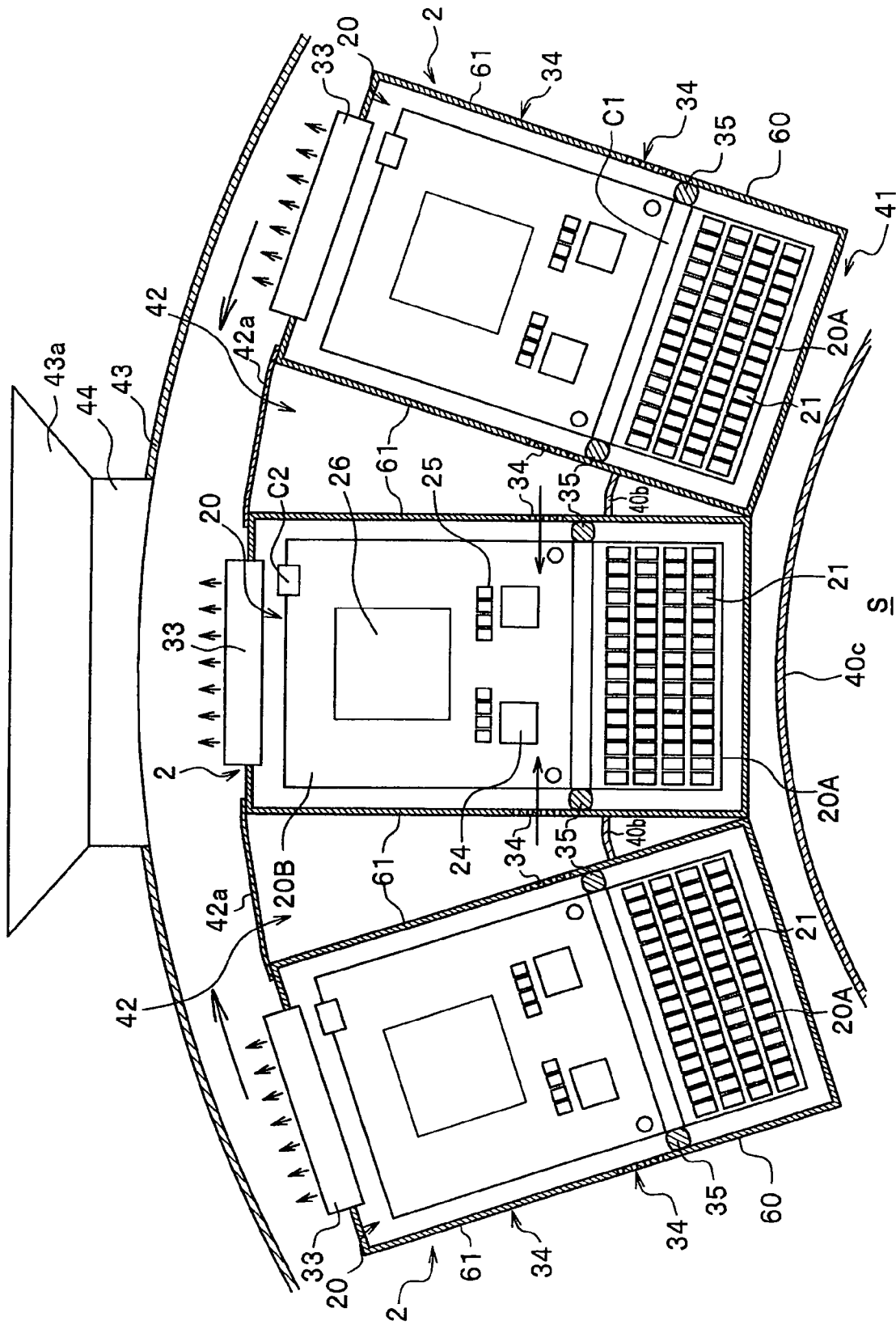

RADIOLOGICAL IMAGING APPARATUS AND ITS COOLING SYSTEM

FIELD OF THE INVENTION

The present invention relates to a radiological imaging apparatus which uses radiation, and, in particular, to a radiological imaging apparatus, which is suitable for a radiological examination with a positron emission tomography apparatus (Positron Emission Computed Tomography, (hereinafter referred to as "PET") and the like, and to its cooling system.

BACKGROUND OF THE INVENTION

Examination technology which utilizes radiation can examine inside a subject in a non-destructive fashion. In particular, the radiological examination technology to a human body includes an X-ray CT, a PET, a single photon emission tomography apparatus (Single Photon Emission Computed Tomography, hereinafter referred to as "SPECT") and the like.

Any of these techonologies is a technology of measuring the physical quantity of an object for examination as an integration value in the direction of flight of radiation, and bringing the integration value thereof into back projection, and thereby calculating and imaging the physical quantity of each voxel in the object to be examined. These technologies require processing of large data, and the rapid progress of computer technology in the recent years has been accompanying provision of rapid and highly detailed images.

A PET as well as an SPECT being a radiological imaging apparatus is a technique capable of detecting functions and metabolism on the level of molecular biology which cannot be detected with an X-ray CT and the like, and is capable of providing function images of a body. The PET is a technique of administering a radiopharmaceutical which has been labeled with a positron-emitting radionuclide such as $^{18}F$, $^{15}O$ and $^{11}C$, of measuring its distribution and of implementing imaging. The pharmaceutical is fluoro-deoxy-glucose (2-[F-18]fluoro-2-deoxy-D-glucose, $^{18}FDG$), etc. and this utilizes that a pharmaceutical is highly concentrated at tumor tissues with saccharometabolism, and is used to identify a tumor site.

The radionuclide taken by a body decays to emit positron ($\beta+$). The emitted positron is coupled with electron and is annihilated, then emits a pair of annihilated γ rays (annihilated γ ray pair) respectively having 511 keV energy. Since these annihilated γ ray pair are emitted in the approximately opposite directions (180°±0.6°), a plurality radiation detectors disposed so as to surround the periphery of the object to be examined detect the annihilated γ ray pair, accumulate data on their emitted directions and thereby can derive projection data. Bringing the projection data into back projection (using the above described filtered back projection method and the like), identification and imaging of emitted position (concentration position of radionuclide) will become feasible.

SPECT is a technique of administrating a radiopharmaceutical which is labeled with single-photon-emitting radionuclide, of measuring distribution thereof and of imaging. From the radiopharmaceutical, a single γ ray with energy around 100 keV is radiated so that this single γ ray is measured with a radiation detector. Since measurement of a single γ ray cannot identify the direction of its flight, an SPECT is provided with a collimator which is inserted in the front plane of a radiation detector, and detects only the γ ray from a specific direction and thereby derives projection data. Likewise the PET, utilizing filtered back projection method and the like, the projection data are brought into back projection to derive image data. Different from the PET, the coincidence due to measurement of a single γ ray is not needed and a smaller number of radiation detectors will do, etc. and therefore the configuration of the apparatus is simple.

The above described radiological imaging apparatus such as conventional PET and SPECT, etc. uses a scintillator as a radiation detector in order to derive an image. A scintillator implements processing to temporarily convert the incident γ ray into a visible light and thereafter to convert further into an electric signal with a photomultiplier (photomul). A scintillator is not abundant in photon generation at the time of visible light conversion and needs a two-step conversion process as described above, therefore giving rise to a problem that it has a low energy resolution and cannot always implement highly accurate imaging. A decrease in energy resolution, in particular, results in inability of quantitative assessment at the time of 3-D imaging of the PET. The reason is that, due to a low energy resolution, the energy threshold of γ ray is obliged to be lowered, resulting in detection of a lot of in-body scattering being noises which increase at the 3-D imaging.

Therefore, in recent years, much attention is being paid to the use of semiconductor detector as a radiation detector for a radiological imaging apparatus. A semiconductor detector converts the incident γ ray directly into an electric signal, and is characterized in a high energy resolution due to abundance in generated electrons and hole pairs.

Normally, it is known that features such as time resolution and energy resolution of a scintillator and a semiconductor detector decrease under environments with a high temperature, and a radiological imaging apparatus comprising a cooling mechanism as means therefor is disclosed (see, for example, JP-A-10-160847 and JP-A-9-276262).

PET examinations detect an annihilated γ ray pair and therefore need to determine coincidentalness of a detected event (carry out coincidence). At detection time of an annihilated γ ray pair, fluctuations exist due to noises and the like in radiation detector and circuit systems, and therefore in order to determine coincidentalness, an allowable specific coincidence time window is provided to determine that the detected two events within this coincidence time window are coincidental.

On the other hand, for a radiological imaging apparatus, in order to improve image qualities and improve quantitativeness of image information, features of time resolution and energy resolution in the above described scintillator and semiconductor detector should be improved.

Improvement of the feature of time resolution will be able to shorten the above described coincidence time window. Then, probability of spontaneously catching a γ ray that is not a true annihilated γ ray pair will be reduced. Since the spontaneously caught γ ray pair (random coincidental events) does not hold true positional information, exclusion of such noise components will improve image qualities and quantitativeness of image information. In addition, improvement of the feature of energy resolution will be able to exclude γ ray due to in-body scattering as described above and improve image qualities and quantitativeness of image information.

However, accompanied by technical advantages offered by radiological imaging apparatuses, increase in number and high density of radiation detectors is in progress, in addition, under the circumstance that the densified state of internally incorporated electronic circuit equipment, etc. accompanied by miniaturization of apparatus is in progress, application of the above described conventional cooling mechanism is unable to sufficiently cool the heat generated from electronic circuit equipment (signal processing apparatus) inclusive of a radiation detector, consequently, there was a concern that features of time resolution and energy resolution decrease.

SUMMARY OF THE INVENTION

An object of the present invention is to provide a radiological imaging apparatus that can restrain the heat generated by a signal processing apparatus from transferring to a radiation detector and a cooling system of radiological imaging apparatus.

In order to solve the above described problems, a radiological imaging apparatus of the present invention is configured by a radiation detector and a signal processing apparatus being provided on a unit substrate, and the heat insulating member which is provided inside the imaging apparatus and separates a first area where a radiation detector is disposed and a second area where a signal processing apparatus is disposed each other. This configuration can completely separate, with the heat insulating member, a second area having a heat generating element from a first area which does not generate heat but is supposed to be kept at a low temperature, and can restrain the heat generated in the signal processing apparatus to be transferred to the radiation detector. Accordingly, time resolution and energy resolution of the semiconductor detector is improved, image quality and quantitativeness of PET image is improved and highly accurate imaging will become feasible.

In addition, since temperature increase of a radiation detector can be restrained, chronological change in the radiation detector can be restrained and the failure rate can be decreased. Accordingly, the characteristics of the radiation detector will be stabilized to improve reliability of the apparatus to enable decrease in running costs.

Moreover, the radiation detector and the signal processing apparatus are provided on a unit substrate consisting of a first and a second substrates and can be configured so as to improve detection accuracy further.

Preferably, configuration includes a cooling apparatus so as to supply coolant. Here, in configuration, the coolant may be supplied from the first area to the second area, or may be supplied to the first area and the second area separately. Moreover, in configuration, it may be supplied only to the second area that has a heat generating element. Taking such configurations, temperature increase in the second area can be restrained, and temperature increase in the radiation detector side in the first area will be remarkably restrained.

Preferably, a semiconductor radiation detector is used, in configuration, to increase detection accuracy. This configuration uses a semiconductor radiation detector, can detect radiations directly and therefore can improve time resolution and energy resolution.

Moreover, the configuration comprises a detector unit provided with a plurality of unit substrates inside a housing member so as to be able to dispose the plurality of detector units around a bed which supports an object to be examined and dispose the heat insulating member inside the housing member. Thus, the configuration with the unit substrate being installed inside the housing member and with the first area and the second area being separated each other by the heat insulating member can effectively restrain temperature increase of a radiation detector. In addition, a portion where the radiation detector is present can be configured so as to be located outside the housing member. Configuring like this, temperature increase in the radiation detector can be restrained more effectively with the heat insulating member.

In addition, a first and a second coolant paths through which the coolant is supplied are formed in the imaging apparatus, the first and the second area parts of the detector unit are respectively disposed in these paths, and thereby the coolant supplied to the paths can implement cooling efficiently in the configuration.

In addition, the cooling system of a radiological imaging apparatus of the present invention comprises a step of separating a first area where a radiation detector on a unit substrate is installed and a second area where a signal processing apparatus is installed each other with a heat insulating member to supply coolant to the second area. Thereby the second area where the signal processing apparatus is disposed can be cooled with a coolant and the radiation detector can be kept at a low temperature state.

It may be configured that the coolant is supplied to the first and the second area separately, or it may be configured that, after the supply to the first area, the coolant is supplied from the first area to the second area. In this case, the coolant supplied from the first area to the second area can efficiently cool the radiation detector and can keep the radiation detector under a low temperature state.

The present invention derives a radiological imaging apparatus that can restrain the heat generated by a signal processing apparatus from transferring to a radiation detector and a cooling system of radiological imaging apparatus.

Other objects, features and advantages of the invention will become apparent from the following description of the embodiments of the invention taken in conjunction with the accompanying drawings.

BRIEF DESCRIPTION OF THE DRAWINGS

FIG. 6A is a sectional view of a detector unit used in a radiological imaging apparatus according to Embodiment 2 as viewed from the front side, and FIG. 6B is a likewise cross-sectional view; and FIG. 7 is a sectional view showing a state with a detector unit having been mounted to a unit support member.

DESCRIPTION OF THE INVENTION

Now, with reference to the drawings as required, a detailed description will be given of a preferred embodiment of a radiological imaging apparatus according to the present invention. In the description of the present embodiment, the PET apparatus is an example of an imaging apparatus configuring a radiological imaging apparatus. Of course, the present invention is not limited to the PET apparatus but is applicable to a radiological imaging apparatus using the other imaging apparatus such as an SPECT, etc.

Embodiment 1

Figure 1:
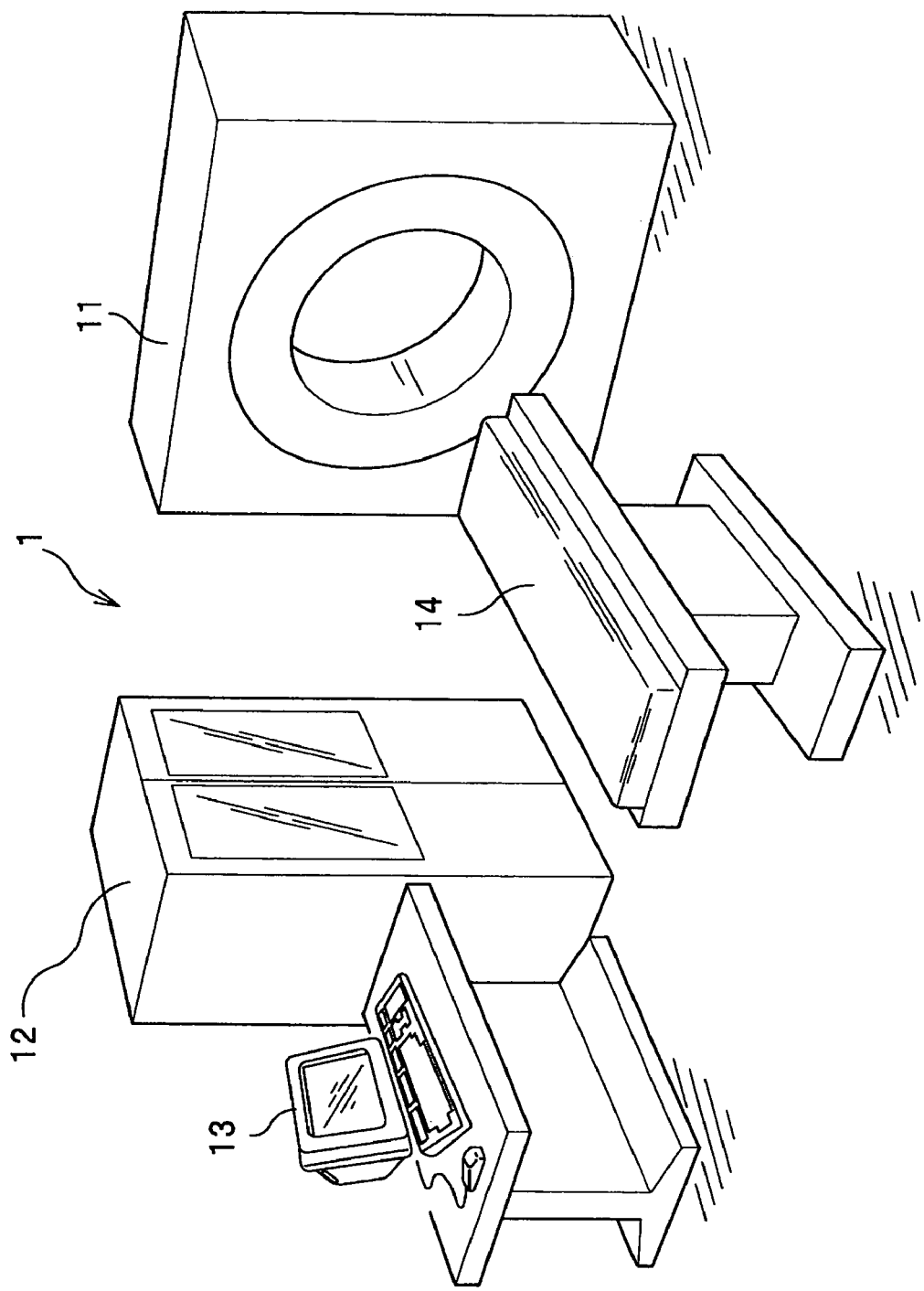
FIG. 1 is a perspective view schematically showing the configuration of a radiological imaging apparatus according to Embodiment 1.

Firstly, with reference to FIG. 1 and FIG. 2, a schematic configuration of a radiological imaging apparatus (PET apparatus 1) of the present embodiment will be described. A PET apparatus 1 comprises an imaging apparatus 11, a data processing apparatus 12 of processing and converting into image data the detection data derived by this imaging apparatus 11 which implements imaging, a display device 13 of displaying, two-dimensionally or three-dimensionally, the image data that this data processing apparatus 12 outputs and a bed 14 on which a subject (object to be examined) H (see FIG. 2) is placed backward-and-forward movably in the direction of body axis.

The imaging apparatus 11 comprises a detector unit 2 having the large number of semiconductor radiation detectors (hereinafter to be referred to as "detector" briefly (see FIGS. 3A and 3B and FIG. 4, hereinafter likewise) and the details will be described below) 21. The detector unit 2 is disposed in the casing 11A of the imaging apparatus 11, and as shown in FIG. 2, so as to surround the bed 14 inserted in the space S of the imaging apparatus 11, a large number of them are disposed in the circumferential direction with the body axis Z of a subject H as the center. The imaging apparatus 11 is further provided with a cooling apparatus 50 (a part of components are depicted in FIG. 2).

To a subject H, a radiopharmaceutical, for example, fluorodeoxy-glucose (FDG) containing $^{18}F$ with a half-life of 110 minutes, is administered. This radiopharmaceutical is concentrated at, for example, a cancerous site (in FIG. 2). As shown in FIG. 2, a pair of γ rays (radiation) generated at annihilation of positron emitted from this FDG are radiated in the direction of 180°±0.6° coincidentally from the body of the subject H. These γ rays are detected by two detectors 21 located in opposite directions separated by 180°. Based on detection signals outputted from these detectors 21, the position of the source (a concentrated site of the radiopharmaceutical) of γ rays inside the body of the subject H is reliably found.

Figure 2:
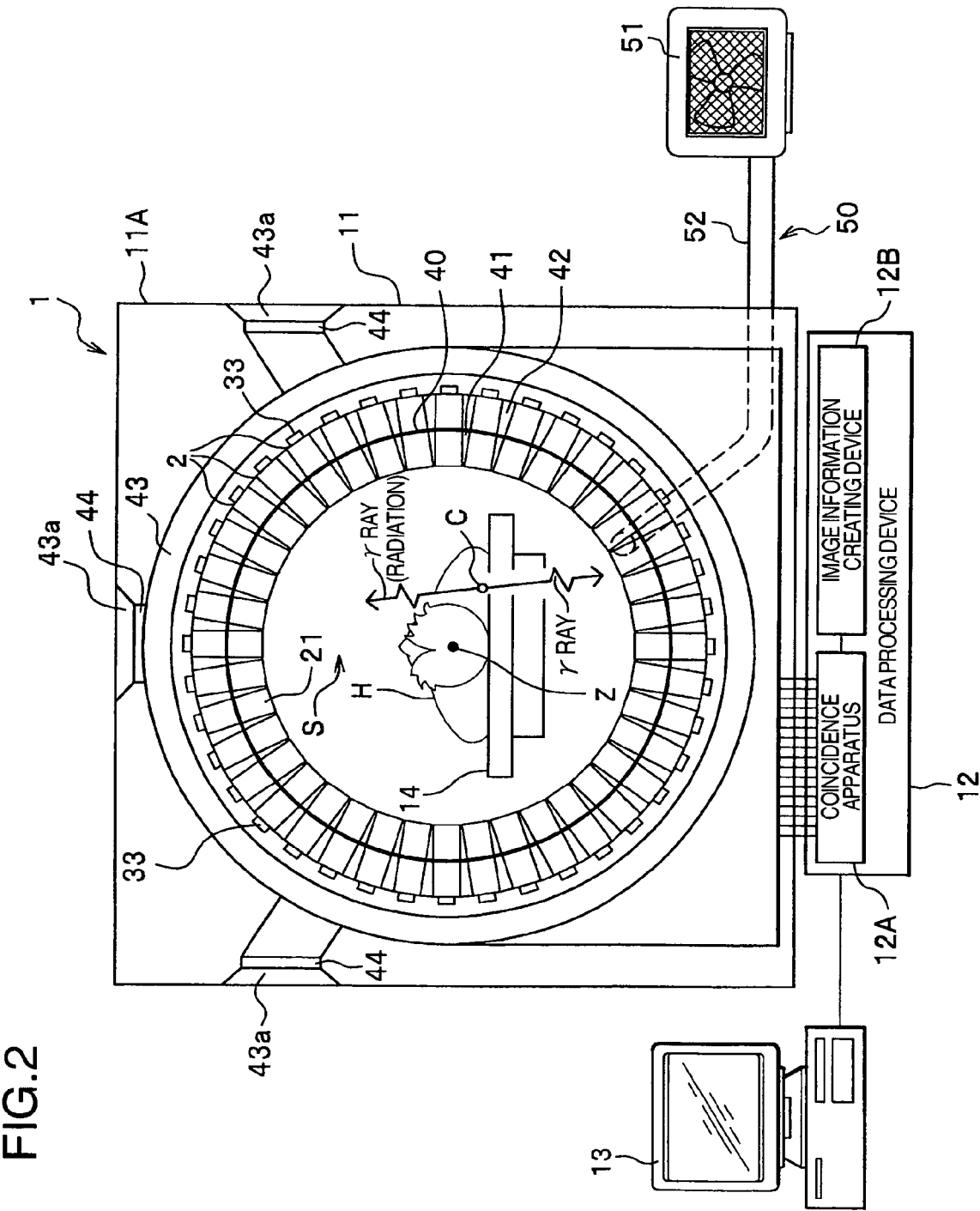
FIG. 2 is a sectional view schematically showing an imaging apparatus in FIG. 1 in the circumferential direction.

The configuration of the detector unit 2 as well as its peripheral parts shown in FIG. 2 is schematic depiction in order to describe their dispositions, and detailed configurations will be described in detail later. The cooling apparatus 50 installed in the imaging apparatus 11 is for cooling the detector 21 of this detector unit 2. In the present embodiment, air is utilized as coolant (cooling medium) of cooling the detector 21. Details of the cooling apparatus 50 will be described later.

The data processing device 12 has, as shown in FIG. 2, a coincidence apparatus 12A and an image information creating device 12B. The data processing device 12 takes data (the later described packet data) outputted from the coupling FPGA (Field Programmable Gate Array) 28 of the built-in coupling substrate 22 (in FIG. 3B) in the detector unit 2. The coincidence apparatus 12A identifies, among these taken data, locations of a pair of detectors 21 which have detected these γ rays from a pair of γ rays from the same source and stores this positional information in a not shown storage device. And the image information creating device 12B creates PET image information (tomogram information) on the subject H based on this identified positional information so as to output this to be displayed on a display device 13.

Specifically, the coincidence apparatus 12A compares the detected time data of a plurality of detected data and determines two data within a coincidence time window length, for example, of 10 ns as effected data. Moreover, the image information creating device 12B collects flight direction data of γ ray pairs from ID of the detector 21 of the above described effective data pairs and implements image reconfiguration from those data to create a PET image. And, the created PET image is outputted onto the display device 13.

Next, details of the main components will be described.

Firstly, with reference to FIGS. 3A and 3B, the detector unit 2 will be described. The detector unit 2 is configured by a plurality of unit substrates 20 being housed in an enclosure 30 being a housing member. Just for a reminder, the imaging apparatus 11 (see FIG. 2) is configured by 60 to 70 units of these detector unit 2 being disposed releasably in the circumferential direction so as to be ready for maintenance check.

The unit substrate 20 includes a detector substrate 20A as a first substrate and a signal processing substrate 20B as a second substrate. The unit substrate 20 are disposed in the enclosure 30 under a state of being arranged in plurality in the direction of the body axis Z of a subject H shown in FIG. 2. The present embodiment is provided with, as shown in FIG. 3B, 15 unit substrates 20 in total.

The detector substrate 20A and the signal processing substrate 20B are provided with an overlapping portion where they overlap each other in the vicinity of the mutual ends with connectors C1 which are present in these overlapped portion being mutually brought into connection, and thereby are mutually connected mechanically and electrically. In this overlapped portion, the detector substrate 20A and the signal processing substrate 20B are mutually coupled releasably with a (not shown) screw. Using such an electrically connecting configuration between the detector substrate 20A and the signal processing substrate 20B, a signal can be transmitted from the detector substrate 20A to the signal processing substrate 20B with low loss. Just for a reminder, less loss will, for example, improve energy resolution as a detector 21.

Thus, electric connection between the detector substrate 20A and the signal processing substrate 20B is implemented with the connector C1, and therefore connection/cancellation of connection (coupling/cancellation of coupling) between the substrates is easy. Accordingly, for example, in the case where a failure occurs in the later described detector 21, analog ASIC 24 or digital ASIC 26, removal of the part with the failure will do. Therefore, any waste such as replacement of a unit substrate 20 in its entirety with a new one due to a failure in a portion can be eliminated and the maintenance costs can be reduced.

Here, the unit substrate 20 is not limited to the above described configuration, but may be configured by one substrate so that the later described respective elements provided in the above described detector substrate 20A and signal processing substrate 20B are provided on this one substrate. Such a unit substrate 20 lacks a connector C1, reduces costs and simplifies assembly.

Figure 3:
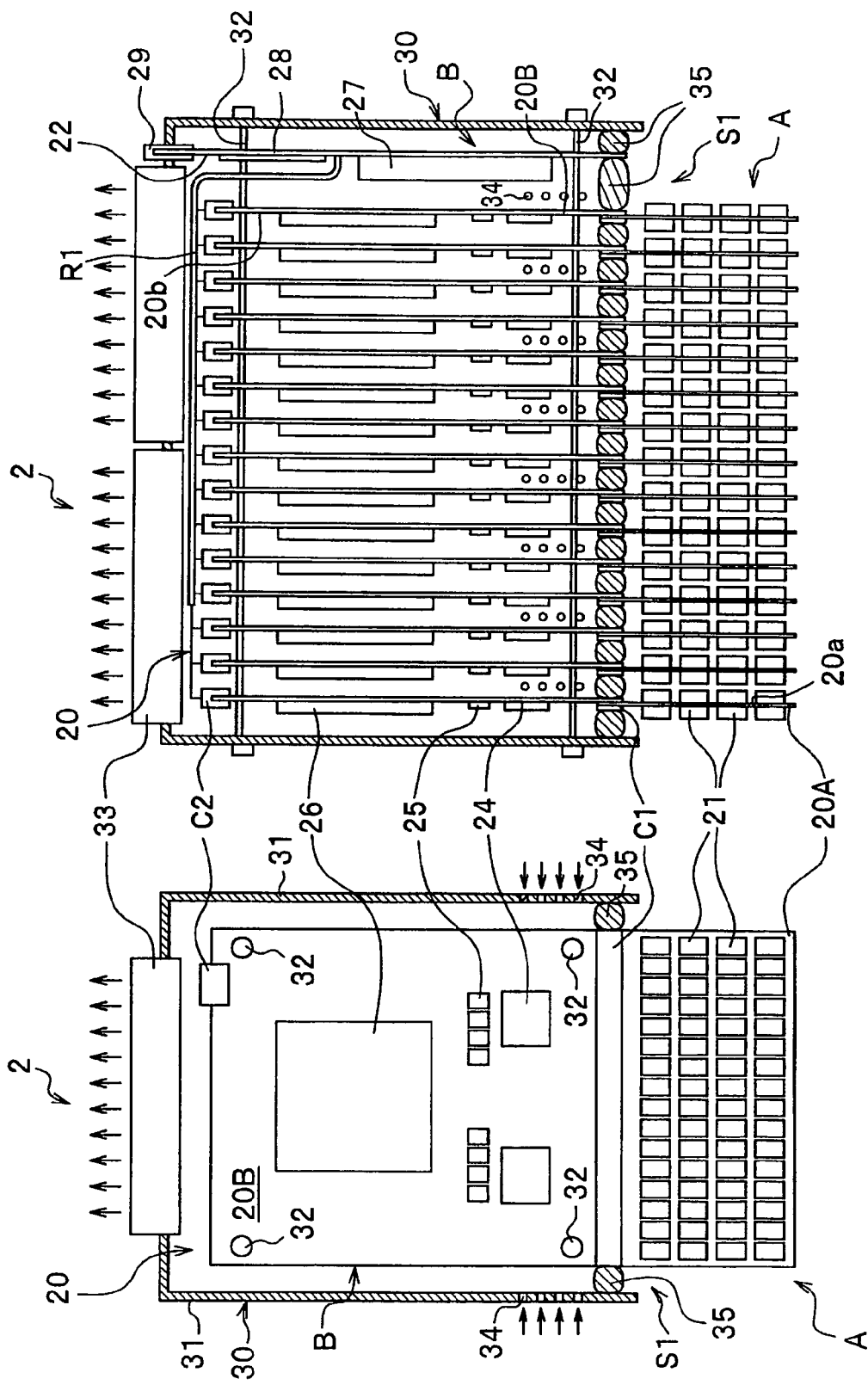
FIG. 3A is a sectional view of a detector unit used in a radiological imaging apparatus according to the present embodiment as viewed from the front side.
FIG. 3B is a likewise cross-sectional view.

At the other end (top end) of the signal processing substrate 20B, a substrate connector C2 is provided, and, as shown in FIG. 3B, the unit substrate 20 is brought into electric connection to the later described coupling substrate 22 disposed in its back side (right hand in FIG. 3B) by a communication line R1 brought into connection via this substrate connector C2.

The detector substrate 20A has, as shown in FIGS. 3A and 3B, a plurality of detectors 21 being arranged in a matrix on the both planes of the substrate main body 20a respectively. In FIG. 3A, 64 units in total of detectors 21 are provided, that is, 16 units in the circumferential direction (circumferential direction in the space S, see FIG. 4) of the imaging apparatus 11 and 4 units in the radius direction (radius direction in the space S, see FIG. 4) of the imaging apparatus 11, per one plane of the substrate main body 20a. In the present embodiment, the detectors 21 are arranged in the circumferential direction with the central axis of the imaging apparatus 11 (substantially coaxial with the body axis Z of the subject H) as the center. In the present embodiment, the pitch of the arrangement of the detectors 21 is made small, the detectors 21 are densely disposed so that the gaps between the mutual detectors 21 are in a narrow state, and thereby high implementation of the detectors 21 on the detector substrate 20A is planned. Accordingly, γ ray detection efficiency of the detector substrate 20A will become improved and examination time is reduced.

The detector 21 has a semiconductor member being sandwiched by the not shown cathode and anode and being laminated. The semiconductor member is composed of any single crystal such as CdTe (cadmium telluride), TlBr (thallium bromide), or GaAs (gallium arsenide). The anode and the cathode are composed of any of Pt (platinum), Au (gold), In (indium), or the like. Configuring the detector 21 like this, charge collecting efficiency will be heightened, the quantity of passing γ rays is made small and interacts (number of counts) between the semiconductor member and the γ ray can be increased (sensitivity is increased). Here, the detector 21 does not necessarily have to be laminated like this, but may be a single layer and may have an appropriate layered structure.

Here, as the installed detector 21 gets numerous, the PET apparatus 1 can detect the γ ray more easily and positional accuracy at the γ ray detection is improved. Therefore, the detectors 21 are preferably disposed densely as described above, and as shown in FIG. 5, the detector unit 2 is preferably disposed in the vicinity of circumferential direction in the casing 11A (see FIG. 2) of the imaging apparatus 11. Employment of such a disposition structure can improve the positional resolution of the derived image.

With such a configuration, each detector 21 detects the γ ray (radiation) of 511 keV used in PET imaging to output an analog signal (γ ray detection signal) corresponding with the energy (energy out of interaction with the semiconductor material) of that γ ray.

Next, the signal processing substrate 20B will be described. In the signal processing substrate 20B, an integrated circuit (analog ASIC24, ADC25 and digital ASIC26) being a signal processing device of processing γ ray detection signals outputted from respective detectors 21 is installed in the substrate main body 20b. These integrated circuits amplify weak γ ray detection signals outputted from the detectors 21 to measure the energy of the detected γ ray and the detection time. And, subject to addition of the preset detection ID, this measured energy and the detection time data are outputted as a packet data (digital data). These outputted packet data are sent from the substrate connector C2 to the coupling FPGA 28 of the coupling substrate 22 through the communication line R1.

The coupling substrate 22 comprises, as shown in FIG. 3B, a high voltage power source 27 being a boosting apparatus for supplying the respective unit substrates 20 with a voltage, a coupling FPGA 28 of aggregating the above described packet data outputted through the substrate connector C2 of each unit substrate 20, and a data transfer apparatus 29 of transmitting these aggregated packet data to the data processing apparatus 12. In the present embodiment, the coupling substrate 22 is arranged like the unit substrate 20, and is disposed at the back side (rightward in FIG. 3B) of the later described enclosure 30. However, without being limited hereto, the coupling substrate 22 can be disposed in the forward side and the like of the enclosure 30.

The high voltage power source 27 is connected to a low voltage power source installed outside the not shown imaging apparatus 11, and the low voltage is boosted to 300 V with a DC-DC converter to be supplied to each detector 21 of each unit substrate 20. In addition, the high voltage power source 27 is mounted on a coupling substrate 22, is disposed in the enclosure 30, and therefore is readily installable to the imaging apparatus 11 by attaching the detector unit 2 to the unit support member 40 (FIG. 2) being a support member.

In the present embodiment, in the imaging apparatus 11, each unit substrate 20 is disposed so that a surface on which each detector 21 is provided in the substrate main body 20a is directed in the longitudinal direction of the bed 14, but this configuration will not establish any limitation. For example, each unit substrate 20 may be disposed so that the surface on which each detector 21 is provided in the substrate main body 20a is directed in the circumferential direction of the imaging apparatus 11.

Next, housing of such a unit substrate 20 as well as a coupling substrate 22 into an enclosure 30 will be described.

The enclosure 30 is a cylinder with rectangular cross-section (preferably, a rectangle), and is attached to a ring-shaped (annular) unit support member 40 (see FIG. 4) provided in the casing 11A of the imaging apparatus 11 in the circumferential direction. The enclosure 30 is, as shown in FIGS. 3A and 3B, formed in such a size that the side parts 31 cover the signal processing substrate 20B of the unit substrate 20 and an opening is formed in the lower end. Thereby, installing the unit substrate 20 in the enclosure 30, the signal processing substate 20B of the unit substrate 20 is disposed in the enclosure 30, but a large part of the detector substrate 20A, that is, the portion where the detector 21 is installed in the detector substrate 20A protrudes downward (to outside) from the opening of the enclosure 30. That is, the entire detector 21 on the substrate main body 20a is not covered by the enclosure 30 but is located outside the enclosure 30. Therefore, as described later, under the state in which the detector unit 2 is attached to the unit support member 40, the detector 21 will be disposed under a state that it is exposed to a first air guiding path 41 inside the unit support member 40.

In the present embodiment, as described above, 15 lines of the unit substrate housed in the enclosure 30 are disposed so as not to overlap each other in the depth direction (in the longitudinal direction of the bed 14) and the coupling substrate 22 is disposed in the back side of the enclosure 30. The unit substrate 20 and the coupling substrate 22 are attached to the enclosure 30 by four substrate fixing bars 32 which extend in the longitudinal direction (the longitudinal direction of the bed 14) of the enclosure 30 and go through them to support.

The top of the enclosure 30 is bent inwardly, and an exhaust unit fan 33 is attached to this portion. This unit fan 33 has a built-in fan rotary-driven with a not shown thin motor and, as described later, plays a role of discharging the air inside the enclosure 30 to the upper exhaust air duct 43 (see FIG. 2) above the enclosure 30. The unit fan 33 is to receive electric power supply from a not shown low voltage power source supplied to the coupling substrate 22 to operate. Here, the unit fan 33 is around-the-clock operating type, but may be configured to operate upon detection of the temperature in the enclosure 30 having reached a predetermined temperature. Configuring like this, consumption of electric power can be restrained.

The opening in the lower part of the enclosure 30 is filled with a heat insulating member 35 so as to fill all the gap S1 formed to the unit substrate 20. In the present embodiment, the heat insulating member 35 is filled (sealed up) in the gaps S1 respectively formed, in the location of the connector C1 of the unit substrate 20, between the mutual unit substrates 20, between the unit substrate 20 and the coupling substrate 22, between the unit substrate 20 and the inner plane of the enclosure 30 and between the coupling substrate 22 and the inner plane of the enclosure 30 so that the opening of the enclosure 30 is blocked. That is, the outside space (a first area A) of the enclosure 30 where all the detectors 21 of the detector substrate 20A are located and the inner space (a second area B) of the enclosure 30 where the signal processing substrate 20B is located are mutually separated by the heat insulating member 35 as a border. Existence of the heat insulating member 35 cuts off the flow of air between the first area A and the second area B mutually through the bottom opening of the enclosure 30. Accordingly, the air heated by heat of the integrated circuit (digital ASIC 26, etc.) of the second area B flows into the first area A to prevent the detector 21 from being heated. Accordingly, the detector 21 will not be exposed to high temperatures.

As a heat insulating member 35, materials with low heat conductivity and with excellent filling nature to the gap S1, for example, urethane can be used. Preferably, urethane should be enclosed with such a member that can shield electro-magnetic waves, for example, a metal sheet. Use of such a member that can shield from electro-magnetic waves can protect the detector 21 from the electro-magnetic waves generated from the integrated circuits (digital ASIC 26 and the like). This can increase time resolution and energy resolution of the detector 21. In addition, for the heat insulating member 35, an elastomeric member, for example, a member with elasticity of rubber and the like is preferably used. Use of such a member facilitates an operation of seal-up of the gap S1 much more, and moreover, can preferably restrain vibrations that might occur in the unit substrate 20 at the time of conveying the PET apparatus 1.

Here, in the above described example, the opening was closed with the heat insulating member 35 filling the periphery of the connector C1 of the unit substrate 20 and around the lower end portion of the coupling substrate 22, but this shows an example, and in configuration, the opening may be closed in any location that can prevent heat from the integrated circuit (digital ASIC 26 etc.) from being transferred to the detector 21 side, for example, in the location in the downward vicinity of the analog ASIC 24.

The side parts 31 of the enclosure 30 are provided with numerous ventholes 34 in order to lead the air being the coolant to inside the enclosure 30 from outside the enclosure 30. The venthole 34 is communicated to the second area B in the enclosure 30. The unit fan 33 is driven and air that is present in the later described second air guiding path 42 outside the enclosure 30 is lead to inside the enclosure 30 without fail. The present embodiment is provided with a plurality of ventholes 34 in a predetermined interval in the longitudinal direction of the enclosure 30. This is to lead a predetermined quantity of air into the enclosure 30 substantially uniformly.

Figure 4:
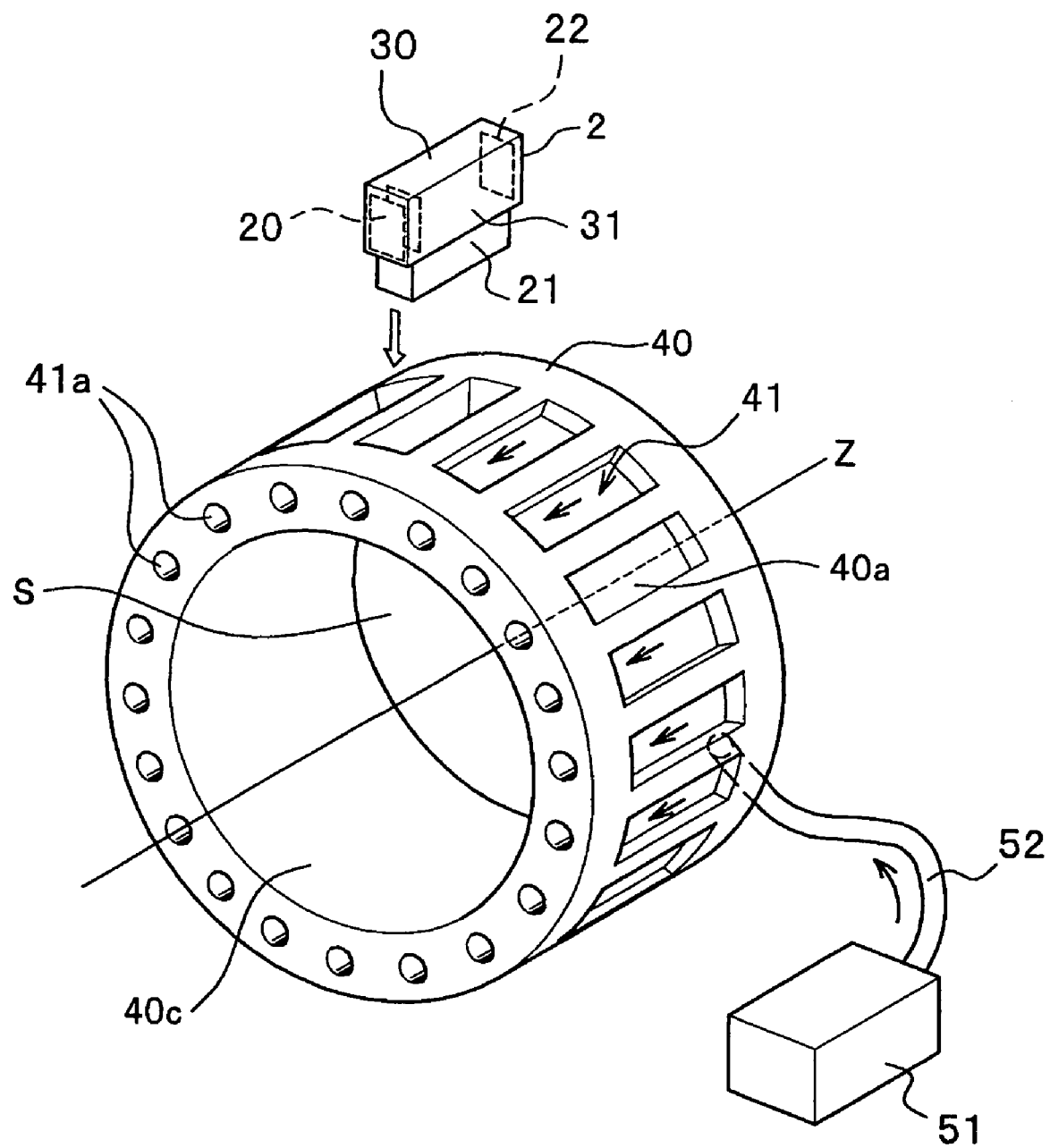
FIG. 4 is a perspective view showing an aspect how a detector unit is mounted to a unit support member of the imaging apparatus.

The detector unit 2 having such an enclosure 30 is attached to the unit support member 40 installed in the casing 11A of the imaging apparatus 11. That is, the detector unit 2 is, as shown in FIG. 4, is inserted from the detector 21 side to the opening 40a formed in the unit support member 40 of the imaging apparatus 11 and is releasably fixed under such a state that the lower end part of the side part 31 of the enclosure 30 is tightly contacted with the opening edge 40b (see FIG. 4 and FIG. 5) of a ring-shaped unit support member 40a. The opening edge 40b is present between mutual openings 40a. Since the lower end part of the enclosure 30 is inserted to a fitting member 55 provided in the exterior surface of the opening edge 40b, positioning on the detector unit 2 in the circumferential direction of the imaging apparatus 11 is implemented. The cylinder plate 40c surrounding the space S is located inside the opening edge 40b and attached to the unit support member 40. As described above, since all the detectors 21 provided to all the unit substrates 20 are located outside the enclosure 30, the detector units 2 are attached to the opening 40a of the unit support member 40, then each detector 21 of the detector unit 2 will be located inside the opening edge 40b, that is, the annular first air guiding path 41 formed between the unit support member 40 and the cylinder plate 40c. Here, the detector unit 2 is fixed with use of a not shown screw and the like. This configures the detector unit 2 releasably to the unit support member 40. Accordingly, an advantage that maintenance and the like can be implemented easily.

Figure 5:
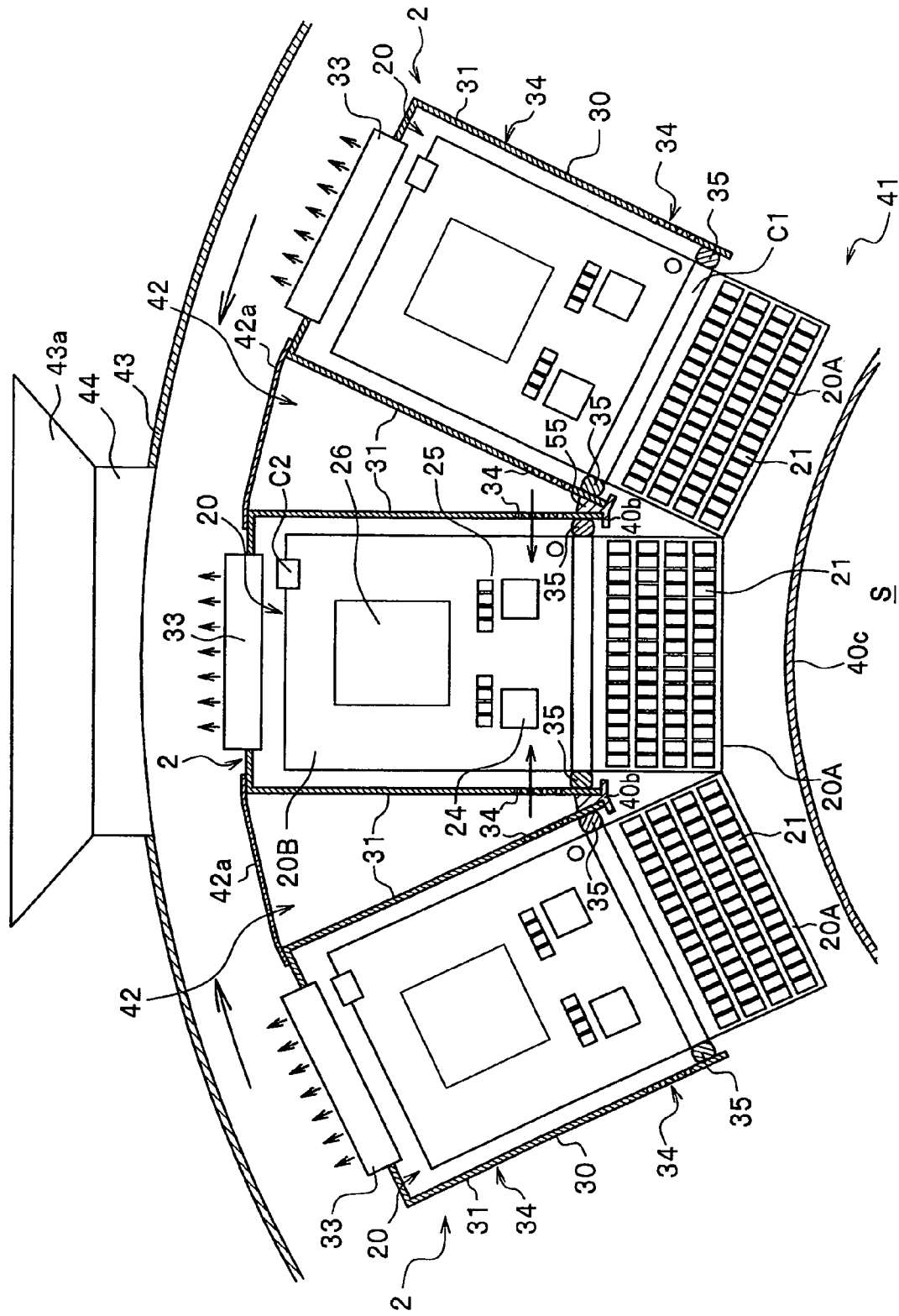
FIG. 5 is a sectional view showing a state with a detector unit having been mounted to a unit support member.

In addition, as shown in FIG. 5, the detector unit 2 does not have side parts 31 (see FIG. 3A) formed in the lower part (a portion located inward from the unit support member 40) and therefore, for that portion, detectors 20A of the adjacent detector units 2 can be disposed close to each other in the circumferential direction. This will make small the dead space between the detector substrates 21 which are adjacent each other in the circumferential direction and the distance between the detectors 20A which are located in the end of these detector substrates 20A respectively and are adjacent each other will get short. This can improve detection sensitivity of radiation. Accordingly, examination time can be shortened.

Next, the cooling apparatus 50 being a characteristic configuration of the present embodiment will be described. The cooling apparatus 50 mainly comprises, as shown in FIG. 2, a blower 51, the first air guiding path (a first coolant path) 41 of the unit support member 40, to which air is introduced from this blower 51, the second air guiding path (a second coolant path) 42 which is provided so as to surround the exterior of the unit support member 40 and to which air is introduced from the first air guiding path 41, an exhaust duct 43 provided so as to surround the exterior of this second air guiding path 42 and an exhaust fan 44 provided in this exhaust duct 43. The annular first air guiding path 41 is, as described above, formed between the opening edge 40b and the cylinder plate 40c. In addition, the second air guiding path 42 is formed in the opening edge 40b, that is, between the mutual enclosures 30 outside the unit support member 40. The first air guiding path 41 and the second air guiding path 42 is formed in the casing 11A, and the exhaust duct 43 as well as the exhaust fan 44 are provided in the casing 11A.

The blower 51 and the duct 52 are disposed outside the casing 11A. The blower 51 is disposed in the side or back of the imaging apparatus 11, etc. so as not to interrupt operations or maintenance, etc. of the imaging apparatus, and sucks air in the room where the imaging apparatus 11 is installed in with a (not shown) built-in fan to supply to the first air guiding path 41 inside the unit support member 40 via the duct 52. To the intake side of the blower 51, a not shown air cleaning filter is attached and the air having passed this air cleaning filter is utilized as cooling air. As the air cleaning filter, a HEPA (High Efficiency Particle Air filter) filter with high dust collecting performance and an electric dust collecting filter and the like can be used. Here, the blower 51 may be provided with not shown cooling means in order to cool the air. In this case, to the duct 52 and the other places where the air flows, a heat insulating member and the like for preventing dew condensation.

To the first air guiding path 41, as shown in FIG. 5, the detector substrates 20A of the unit substrate 20 are disposed in a predetermined interval in the circumferential direction. As shown in FIG. 4, to the back portion of the unit support member 40, the duct 52 from the blower 51 is connected (depicted with a broken line), and to the front portion of the unit support member 40 is provided with a plurality of through holes 41a which are communicated to the first air guiding path 41. Thereby, the air from the blower 51 flows from the back side (the side where the duct 52 is connected) inside the first air guiding path 41 to the front side (the side where the through hole 41a is provided) and is discharged from the through hole 41a.

The through hole 41a is communicated to the second air guiding path 42, and thereby, the air from the first air guiding path 41 is introduced to the second air guiding path 42. Details of the second air guiding path 42 will be described with reference to FIG. 5. The second air guiding path 42 is formed by the space partitioned by respective side parts 31 of the adjacent enclosures 30, a ceiling plate 42a bridging those enclosures 30 and opening edges 40b of the unit support member 40, and is located between the respective detector units 2. To the second air guiding path 42, air from the first air guiding path 41 is arranged to be introduced through the through hole 41a (see FIG. 4). Here, in the portion which is communicated to the through hole 41a of the second air guiding path 42, a not shown path for introducing air from the through hole 41a to the second air guiding path 42 is formed inside the casing 11A. In addition, the opening (the gap between the side parts 31 and 31 in the back end of the enclosure 30) in the back side of the second air guiding path 42 to be located in the opposite side hereof is closed with a not shown plate member. Here, removal of one of the detector units 2 from the unit support member 40 for a maintenance operation, etc. can be implemented simply by removing the ceiling plate 42a and not shown plate member and the like attached to the detector unit 2 to be removed. Accordingly, complicated operations such as removal of the second air guiding path 42 in its entirety are not required and maintenance operation, etc. can be implemented in a simplified fashion.

The second air guiding path 42 is communicated to the interior of the enclosure 30 though a plurality of through holes 34 provided in the side parts 31 of the enclosure 30. Coupled with the drive of the unit fan 33 of the enclosure 30, to inside the enclosure 30, air from the second air guiding path 42 is introduced. The exhaust air duct 43 is communicated to the interior of the enclosure 30 through the unit fan 33, and the unit fan 33 is driven so that the air from inside the enclosure 30 is discharged to the exhaust air duct 43. The exhaust air duct 43 is provided with three exhaust ports 43a opened in the room where the imaging apparatus 11 is installed, and through the exhaust fan 44 provided to each exhaust port 43a, the air inside the exhaust air duct 43 is discharged inside the room.

Here, the present embodiment is configured to suck air in the room where the imaging apparatus 11 is installed in to utilize as cooled air and discharge again into the room after cooling, but may be configured to suck air from outside the room in and to discharge the air after cooling again outside the room.

Next, cooling with such a cooling apparatus 50 will be described. When the not shown power source switch of the imaging apparatus 11 is operated to supply the imaging apparatus 11 with electric power, in association with operation of the imaging apparatus 11, the blower 51 operates. Then, air inside the room is ventilated to the cooling air from the blower 51 to the first air guiding path 41 of the unit support member 40 through the duct 52 (a step of supplying the first area A with the cooling air), and the ventilated cooled air passes from the back side toward the front side in the first air guiding path 41. Inside the first air guiding path 41, the detector 21 of the unit substrate 20 retained in the detector unit 2 is disposed under an exposed state, and therefore each detector 21 is cooled with the cooling air ventilated into the first air guiding path 41. Here, originally the detector 21 is not of a nature to generate heat, but, for example, even if such an event that the heat from the signal processing substrate 20B side is transferred through the connector C1 being a connecting part occurs, the detector 21 can be remarkably restrained from being heated with that heat. Accordingly, time resolution and energy resolution of the detector 21 can be improved.

Thereafter, the air having passed the first air guiding path 41 is introduced from the through hole 41a to the second air guiding path 42, and introduced inside the enclosure 30 through the through hole 34 provided in the side parts 31 of the enclosure 30 (a step of supplying, from the first area to the second area B, the cooling air (coolant) supplied to the first air guiding path A). Thereby, the interior of the enclosure 30 is cooled with the cooling air, the integrated circuits (digital ASIC 26, etc.) are cooled, and increase in temperature of the second area B is restrained so that thermal runaway of the signal process system can be prevented. Accordingly, reliability of an apparatus is improved.

Thus, the cooling air is supplied from the first area A where the detector 21 is disposed to the second area B so that the air that has cooled the detector 21 cools the integrated circuits (digital ASIC 26, etc.), and therefore through a series of sequence, the detector 21 and the integrated circuits (digital ASIC 26, etc.) will be cooled efficiently. Here, the quantity of air supply supplied by the blower 51 is set so as to be able to be cooled to such an extent that will not give rise to thermal runaway or destruction of the integrated circuits (digital ASIC 26, etc.) and so that the detector 21 is kept at a low temperature, taking the number of the detectors 21 (the number of the unit substrates 20) the state of temperature increase of the integrated circuits (digital ASIC 26, etc.) and the like into consideration.

The cooling air supplied inside the enclosure 30 is forcibly discharged to the exhaust air duct 43 with the unit fan 33. The air subject to cooling that has been discharged to the exhaust duct 43 is discharged to the interior of the room from the exhaust port 43a with the exhaust fan 44 provided in the exhaust port 43a. As described above, cooling with cooling air by the cooling apparatus 50 is implemented.

Since the detector 21 with CdTe as the semiconductor material used in the present embodiment generates charge in reaction to light, light shielding is implemented so that no light intrudes from outside to radiate onto these detectors 21. Specifically, the enclosure 30 shown in FIG. 4 and the unit support member 40 are configured by materials having a light shielding nature such as aluminum or aluminum alloy, and is configured so as to eliminate any gap where lights intrude, including the portion where the both parties are fitted.

The light that intrudes from the direction of the space S can be firmly prevented from reaching the detector 21 by disposing the cylinder plate 40c so that its external periphery surface is located in the vicinity of the free end (lower end) of the detector substrate 20A. In addition, the cylinder plate 40c is configured by aluminum alloy (or aluminum) so that a light shielding nature can be improved. Moreover, another method of protection against the light which intrudes from the direction of the space S may be configured to cover the enclosure 30 with a not shown light shielding cover etc., or the detector 21 may be coated with a light shielding member so that a light shielding film is formed instead of a light shielding cover and the like.

In addition, the exhaust air duct 43 may be divided in the circumferential direction of the exhaust air duct 43 so that each space of the respective divided exhaust air duct 43 is provided with an exhaust fan 44. Providing exhaust fans 44 independently like this, more efficient exhaust discharge can be implemented and smooth ventilation of the cooling air can be realized. In addition, the exhaust duct 43 may be configured by division in bisection, quadrisection or more.

Advantages in the present embodiment will be described as follows.

(1) According to this radiological imaging apparatus, the unit substrate 20 is comprised by detector substrate 20A (first substrate) in which the detector 21 is installed and a signal processing substrate 20B (second substrate) in which the signal processing apparatus is installed, the first area A where the detector 21 is disposed and the second area B where the signal processing apparatus is disposed being mutually separated, and therefore the heat generated by the integrated circuit (digital ASIC26 and the like) is cut off with the heat insulating member 35 and can be remarkably restrained from being transferred to the detector 21 side. Thereby, increase in temperature of the detector 21 in the first area A can be remarkably restrained and the detector 21 can be kept at a low temperature. Thereby, time resolution and energy resolution can be improved. In addition, since time resolution can be improved, coincidence time window of γ ray will be able to be shortened and probability of spontaneously catching a γ ray is reduced. Moreover, since energy resolution can be improved, in-body scattering will be removed (noises will be reduced). Accordingly, a radiological imaging apparatus that can implement highly accurate imaging with image qualities and quantitativeness of PET image being improved is derived.

Moreover, since the detector substrate 20A and the signal processing substrate 20B are coupled through the connector C1, the heat from the signal processing substrate 20B side will be hardly transferred to the detector substrate 20A side directly, and temperature increase in the detector 21 installed in the detector substrate 20A can be remarkably restrained. Thereby, a radiological imaging apparatus will derive with more improved time resolution and energy resolution is derived.

In addition, since temperature increase of the detector 21 can be restrained, chronological change in the detector 21 can be restrained and the failure rate can be decreased. Accordingly, the characteristics of the detector 21 will be stabilized to improve reliability of the imaging apparatus 11 to enable decrease in running costs.

Moreover, the detector 21 will be kept at a low temperature, such an advantage is derived that the voltage supplied from the high voltage power source 27 of the coupling substrate 22 is stabilized.

(2) According to this radiological imaging apparatus, the first and the second areas A and B can be suitably cooled with the cooling air supplied to the cooling apparatus 50. Moreover, since the cooling air is supplied from the first area A to the second area B with the cooling apparatus 50, after the detector 21 side being the side with low temperature without any heat generating element is cooled, the integrated circuit (digital SIC26 or the like) side being the side with high temperature is cooled. Thereby, coupled with an advantage that can restrain temperature increase in the detector 21 with the above described heat insulating member 35, the temperature increase in the detector 21 can be restrained more.

(3) According to this radiological imaging apparatus, the detector unit 2 is configured by a plurality of unit substrate 20 being housed in the enclosure 30, a plurality of detector units 2 are configured to be disposed in the circumferential direction of the ring-shaped unit support member 40 to which the bed 14 supporting the subject H is inserted, and therefore high implementation of the detectors 21 can be planned, and a radiological imaging apparatus with improved spatial resolution and shortened examination time due to the substantial improvement of sensitivity is derived. In particular, since the portion of the detector substrate 20A where the detector 21 is present is disposed outside the enclosure 30, the gap between the mutual unit substrates 20 of the adjacent detector units 2 can be narrowed, and the detectors 21 can be disposed more densely in the circumferential direction of the imaging apparatus 11. Accordingly, detection sensitivity of γ rays in the imaging apparatus 11 can be improved and examination time can be shortened.

Since the portion of the detector substrate 20A where the detector 21 is present is disposed outside the enclosure 30, the cooling efficiency of the detector 21 is improved compared with the configuration in FIG. 7.

In addition, since the detector unit 2 is held and fixed by the unit support member 40, the detector unit 2 is ready for attachment and removal and is highly maintainable.

(4) According to this radiological imaging apparatus, since the first area A where the detector 21 is disposed is separated from the second area B each other with the heat insulating member 35 and is disposed in the lower part of the detector unit 2 under an exposed state, a radiological imaging apparatus will derive with more improved time resolution and energy resolution is derived.

(5) According to this radiological imaging apparatus, since the first air guiding path 41 for cooling the detector 21 is formed in the unit support member 40, the unit support member 40 can be used effectively as a cooling air supply path, and the mechanism for implementing cooling can be configured simply.

(6) According to this radiological imaging apparatus, since the semiconductor radiation detector is used as a detector 21, energy resolution is improved, γ rays due to in-body scattering can be removed. Accordingly, a radiological imaging apparatus that can implement highly accurate imaging is derived. In particular, in 3D imaging, increase in γ rays due to in-body scattering is restrained so that intensive improvement of image quality of PET images is planned to enable quantitative examination.

(7) According to this radiological imaging apparatus, since the semiconductor radiation detector is used as a detector 21, positional resolution is improved. Since a conventional scintillator amplifies signals of several tens of scintillators with one photomul, to calculate the scintillator position detected with calculation of the center, positional resolution is susceptible to deterioration. In addition, since a photomul is used, scintillator miniaturization is limited.

On the other hand, in the radiological imaging apparatus of the present embodiment, amplifier circuit is formed in each detector 21, positional resolution is not deteriorated. Moreover, since a signal processing apparatus is used with ASIC (24, 26) etc., miniaturization of the detector 21 is easy and further improvement of positional resolution is feasible.

(8) Since this radiological imaging apparatus uses a semiconductor radiation detector as the detector 21 to use ASIC (24, 26) for signal process thereof, miniaturization in the vicinity of the detector is realized in comparison with the photomul used in a scintillator. Accordingly, enlargement of the first air guiding path 41 can be prevented and, despite the configuration comprising the cooling apparatus 50, miniaturization of the imaging apparatus 11 can be planned. In addition, since the detector 21 and the integrated circuit (digital ASIC26 etc.) are disposed in good order on the unit substrate 20, miniaturization of the detector unit 2 becomes feasible, and thereby, miniaturization of the second air guiding path 42 will become feasible, and, despite the configuration comprising the cooling apparatus 50, miniaturization of the imaging apparatus 11 can be planned.

(9) The unit support member 40 is a member of supporting the detector unit 2 and also is a member of separating the first air guiding path 41 from the second air guiding path 42. Therefore, it is not necessary to provide respectively the member of supporting the detector unit 2 and a member of separating the first air guiding path 41 from the second air guiding path 42, and the structure of the imaging apparatus 11 can be simplified. The heat insulating member 35 is not only a member of separating the first area A from the second area B but also a member of separating the first air guiding path 41 from the second air guiding path 42. Installation of this heat insulating member 35 simplifies the structure of the imaging apparatus 11 further.

Embodiment 2

A PET apparatus 10 as a radiological imaging apparatus being another embodiment will be described. The radiological imaging apparatus of the present embodiment is, as shown in FIGS. 6A, 6B and 7, different from Embodiment 1 in the point that the enclosure 60 being a housing member of the detector unit 2 is formed in such a size to cover the unit substrate 20 in its entirety. Specifically, as shown in the said drawing, the enclosure 60 is in a box-type shape having a bottom 60a, and no opening is provided in the lower part as in the enclosure 30 (see FIGS. 3A and 3B) described in Embodiment 1. That is, inside the enclosure 60, a first area A and a second area B partitioned with a heat insulating member 35 are formed.

In the present embodiment, the lower part of the enclosure 60 is disposed in the first air guiding path 41, and thereby with cooling air supplied to the first air guiding path 41, the enclosure 60 is cooled. That is, it is configured that, cooling the enclosure 60, temperature increase of the detector 21 housed therein is restrained. The first air guiding path 41 is communicated to the second air guiding path 42 through the through hole 41a (see FIG. 4) like Embodiment 1, and the cooling air having passed the first air guiding path 41 is supplied to the second air guiding path 42 through the through hole 41a.

In addition, in configuration, the side parts 61 of the enclosure 60 are located in the second air guiding path 42, and through the ventholes 34 formed in the side parts 61, the second air guiding path 42 is communicated to the second area B inside the enclosure 60. Thereby, the cooling air supplied to the second air guiding path 42 is supplied to the second area B through the ventholes 34. The cooling air supplied to the second area B is discharged inside the exhaust air duct 43 with the unit fan 33 provided in the upper part of the enclosure 60.

According to such a PET apparatus 10, since temperature increase in the detector 21 will be effectively restrained to keep the detector 21 at a low temperature state, time resolution and energy resolution of the detector 21 is improved.

In configuration, the lower part (bottom 60a etc.) of the enclosure 60 may be provided with a not shown insertion through hole so that the cooling air supplied to the first air guiding path 41 flows spontaneously into the first area A from the lower part of the enclosure 60 to cool the first area A.

In addition, in configuration, the opening edge 40b partitioning the first air guiding path 41 from the second air guiding path 42 may be provided with through holes to bring the first air guiding path 41 and the second air guiding path 42 into communication. Moreover, in configuration, the opening edge 40b may be deleted so that the first air guiding path 41 and the second air guiding path 42 become an integral air guiding path.

The present embodiment has the advantages described below in addition to the above described advantages (1) to (9).

(10) According to the radiological imaging apparatus of the present embodiment, the unit substrate 20 is configured to be housed in its entirety into the enclosure 60, and therefore is excellent in the light shielding nature, deriving an advantage that, coupled with the cooling effects by the cooling apparatus 50, time resolution and energy resolution of the detector 21 is improved further more.

In the above described respective embodiments, mounting (housing) onto the imaging apparatus 11 of the detector unit 2 is not limited to those with the above described unit support member 40, but any means and system of mounting and housing may be used.

In addition, the above described embodiment is configured that the cooling air is supplied from the first area A to the second area B, but will not be limited thereto, and may be configured that, for example, the cooling air is supplied only to the second area B where the integrated circuit (digital ASIC 26 etc.) is installed with the cooling apparatus 50. Taking such a configuration, the second area B having a heat generating element will be cooled directly with the cooling air, and therefore, also in this case, coupled with the air ventilation shielding effect by the heat insulating member, heat will be hardly transferred to the first area A side where the detector 21 is installed and temperature increase of the detector 21 can be effectively restrained. Thereby, the detector 21 will become maintainable at a low temperature state so that time resolution and energy resolution of the detector 21 can be improved, and a radiological imaging apparatus capable of implementing highly accurate imaging is derived. In addition, troubles in the integrated circuits and the like which are disposed in the second area B can be made less so that reliability of the imaging apparatus 11 is improved and maintenance costs and the like can be decreased.

Moreover, it may be configured that the cooling air is respectively and individually supplied to the first and the second areas A and B. Such configuration can cool the first and the second areas A and B individually, and temperature management each on the first and the second areas A and B can be implemented severely. Thereby, it will become possible, for example, to keep the detector 21 at a state equal to the room temperature and hold the temperature in the second area B at 80° C. or lower. Accordingly, the detector 21 can be maintained at a low temperature state without fail.

In this case, two cooling apparatuses (the first and the second cooling apparatuses) may be provided respectively to the first and the second areas A and B. Such configuration can further improve the nature susceptible to temperature control, and can closely manage temperature of the first and the second areas A and B. In addition, in order to cool the detector 21, the second area B can be prevented from being cooled more than necessary so as to improve the cooling efficiency. Moreover, despite the configuration comprising two independent cooling apparatuses, an advantage that the running costs can be restrained is derived.

In addition, as the coolant, without being limited to air, fluid such as water etc. can be utilized. In this case, a component member such as a water jacket etc., to which cooling water for cooling purpose is supplied, is disposed in the space inside the second area B or the integrated circuit (digital ASIC 26 etc.), and thereby cooling can be implemented.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A radiological imaging apparatus comprising:
a bed which supports an object to be examined; and
an imaging apparatus,
wherein said imaging apparatus has unit substrates each including a plurality of radiation detectors and signal processing apparatuses to which detection signals of said radiation detectors are inputted, and
said imaging apparatus is provided with a heat insulating member separating a first area where said radiation detectors are disposed from a second area where said signal processing apparatuses are disposed, both of which are formed inside said imaging apparatus; and
wherein:
said radiological imaging apparatus further comprises a cooling apparatus for supplying coolant to said second area,
said radiation detectors are semiconductor radiation detectors,
said first area is formed with a housing member having no ventholes and said heat insulating member, and
said second area is formed with a housing member having ventholes and said heat insulating member.

2. The radiological imaging apparatus according to claim 1, comprising a detector unit provided with a plurality of said unit substrates inside a housing member, wherein a plurality of said detector units are disposed around a bed which supports an object to be examined and said heat insulating member is disposed inside said housing member.

3. The radiological imaging apparatus according to claim 2, wherein:
said imaging apparatus comprises an annular support member surrounding said bed and said plurality of detector units are attached to said support member;
said cooling apparatus has a first coolant path which is formed inward from said support member and inside said imaging apparatus and a second coolant path, which is formed outward from said support member and inside said imaging apparatus, and which is provided with said coolant inside said first coolant path; and
a part of said first area of said detector unit is disposed inside said first coolant path and a part of said second area of said detector unit is disposed inside said second coolant path.

4. A radiological imaging apparatus comprising:
a bed which supports an object to be examined; and
an imaging apparatus,
wherein said imaging apparatus has unit substrates each including a plurality of radiation detectors and signal processing apparatuses to which detection signals of said radiation detectors are inputted, and
said imaging apparatus is provided with a heat insulating member separating a first area where said radiation detectors are disposed from a second area where said signal processing apparatuses are disposed, both of which are formed inside said imaging apparatus,
wherein said radiological imaging apparatus comprises a cooling apparatus having a path for supplying coolant from said first area to said second area,
wherein said radiation detectors are semiconductor radiation detectors,
wherein said radiological imaging apparatus comprises a detector unit provided with a plurality of said unit substrates inside a housing member, wherein a plurality of said detector units are disposed around a bed which supports an object to be examined and said heat insulating member is disposed inside said housing member,
wherein a part where said radiation detector is present is disposed outside said housing member, and
wherein:
said imaging apparatus comprises an annular support member surrounding said bed and said plurality of detector units are attached to said support member;
said cooling apparatus has a first coolant path which is formed inward from said support member and inside said imaging apparatus and a second coolant path, which is formed outward from said support member and inside said imaging apparatus, and which is provided with said coolant inside said first coolant path; and
a part of said second area of said detector unit is disposed inside said second coolant path and a part, in which said radiation detector is present, of said unit substrate is located outside said housing member and is disposed inside said first coolant path, and
said plurality of detector units is arranged around said bed in a circumferential direction.

5. A radiological imaging apparatus comprising:
a bed which supports an object to be examined; and
imaging apparatus,
wherein:
said imaging apparatus has unit substrates each including a plurality of radiation detectors and signal processing apparatuses to which detection signals of said radiation detectors are inputted,
said imaging apparatus is provided with a heat insulating member separating a first area where said radiation detectors are disposed from a second area where said signal processing apparatuses are disposed, both of which are formed inside said imaging apparatus,
said radiation detectors are semiconductor radiation detectors,
said imaging apparatus comprises a detector unit provided with a plurality of said unit substrates inside a housing member, wherein a plurality of said detector units are disposed around a bed which supports an object to be examined and said heat insulating member is disposed inside said housing member,
a part where said radiation detector is present is disposed outside said housing member,
said radiological imaging apparatus comprises a first cooling apparatus for supplying coolant to said first area and a second cooling apparatus for supplying coolant to said second area, and
said plurality of said detector units are disposed around said bed in a circumferential direction.

6. A radiological imaging apparatus comprising:
a bed which supports an object to be examined; and
an imaging apparatus,
wherein:
said imaging apparatus has unit substrates each including a plurality of radiation detectors and signal processing apparatuses to which detection signals of said radiation detectors are inputted,
said imaging apparatus is provided with a heat insulating member separating a first area where said radiation detectors are disposed from a second area where said signal processing apparatuses are disposed, both of which are formed inside said imaging apparatus, said radiation detectors are semiconductor radiation detectors, said radiological imaging apparatus comprises a detector unit provided with a plurality of said unit substrates inside a housing member, wherein a plurality of said detector units are disposed around a bed which supports an object to be examined and said heat insulating member is disposed inside said housing member, a part where said radiation detector is present is disposed outside said housing member, said first area is formed with a housing member having no ventholes and said heat insulating member, and said second area is formed with a housing member having ventholes and said heat insulating member.

* * * * *